(12) United States Patent
Buchalter et al.

(10) Patent No.: US 9,408,671 B2
(45) Date of Patent: Aug. 9, 2016

(54) BIOPSY GRID

(75) Inventors: Neal Buchalter, Short Hills, NJ (US); Kenneth M. Zinn, Westport, CT (US)

(73) Assignee: PARKER LABORATORIES, INC., Fairfield, NJ (US)

( * ) Notice: Subject to any disclaimer, the term of this patent is extended or adjusted under 35 U.S.C. 154(b) by 0 days.

(21) Appl. No.: 13/314,972

(22) Filed: Dec. 8, 2011

(65) Prior Publication Data

US 2013/0150703 A1    Jun. 13, 2013

(51) Int. Cl.
| | |
|---|---|
| *G01B 3/14* | (2006.01) |
| *H05G 1/28* | (2006.01) |
| *A61B 19/00* | (2006.01) |
| *A61M 5/42* | (2006.01) |
| *A61B 6/04* | (2006.01) |
| *A61B 6/00* | (2006.01) |
| *A61B 17/00* | (2006.01) |
| *A61B 10/02* | (2006.01) |

(52) U.S. Cl.
CPC ............... *A61B 19/54* (2013.01); *A61B 6/0492* (2013.01); *A61B 6/481* (2013.01); *A61M 5/427* (2013.01); *A61B 10/0233* (2013.01); *A61B 2017/00951* (2013.01); *A61B 2019/5454* (2013.01); *A61B 2019/5466* (2013.01)

(58) Field of Classification Search
CPC ........... A61B 19/54; A61B 2019/5454; A61B 2019/5466; A61B 6/481; A61B 6/0492; A61B 10/0233; A61B 2017/00951; A61M 5/427
See application file for complete search history.

(56) References Cited

U.S. PATENT DOCUMENTS

| | | | |
|---|---|---|---|
| 3,547,121 | A | 12/1970 | Cherry |
| 4,774,957 | A | 10/1988 | Nambu et al. |
| 4,860,331 | A | 8/1989 | Williams et al. |
| 4,916,170 | A | 4/1990 | Nambu et al. |
| 4,985,019 | A | 1/1991 | Michelson |
| 5,052,035 | A | 9/1991 | Krupnick |
| 5,285,785 | A | 2/1994 | Meyer |
| 5,368,030 | A | 11/1994 | Zinreich et al. |
| 5,383,234 | A | 1/1995 | Russell |
| 5,407,440 | A | 4/1995 | Zinreich et al. |
| 5,427,099 | A | 6/1995 | Adams |

(Continued)

FOREIGN PATENT DOCUMENTS

| | | |
|---|---|---|
| JP | 05068678 | 9/1993 |
| JP | 08238248 | 9/1996 |

(Continued)

OTHER PUBLICATIONS

International Search Report and Written Opinion of PCT Application No. PCT/US2012/068141, mailed Apr. 9, 2013, 12 pages.

(Continued)

*Primary Examiner* — Elmer Chao
(74) *Attorney, Agent, or Firm* — Kilpatrick Townsend & Stockton LLP

(57) ABSTRACT

A biopsy grid is provided that is useful in medical imaging. The biopsy grid comprises a hydrogel layer containing a mixture of contrast agents that are visible in images from X-ray, CT scans, MRI, and/or positron emission tomographs. The hydrogel mixture is attached to a frame having a silicone coated release liner and an adhesive layer. The hydrogel layer is cut into strips that serve as markers in an image. The biopsy grid can be used to locate the position of the marker relative to a tissue of interest in a medical image.

15 Claims, 3 Drawing Sheets

(56) References Cited

U.S. PATENT DOCUMENTS

| | | | |
|---|---|---|---|
| 5,469,847 A * | 11/1995 | Zinreich et al. | 600/414 |
| 5,690,120 A | 11/1997 | Jacobsen et al. | |
| 5,702,128 A | 12/1997 | Maxim et al. | |
| 5,908,410 A | 6/1999 | Weber et al. | |
| 5,961,455 A | 10/1999 | Daum et al. | |
| RE36,461 E | 12/1999 | Russell et al. | |
| 6,200,258 B1 | 3/2001 | Slater et al. | |
| 6,356,621 B1 | 3/2002 | Furumori et al. | |
| 6,419,680 B1 | 7/2002 | Cosman et al. | |
| 6,714,628 B2 | 3/2004 | Broyles et al. | |
| D503,980 S | 4/2005 | Sayre et al. | |
| 6,928,146 B2 | 8/2005 | Broyles et al. | |
| 7,086,172 B2 * | 8/2006 | Gunnar | 33/563 |
| 7,127,040 B2 | 10/2006 | Sayre et al. | |
| 7,263,159 B2 | 8/2007 | Russell | |
| 7,494,497 B2 | 2/2009 | Weber | |
| D590,948 S | 4/2009 | Archambault | |
| D602,590 S | 10/2009 | Dzierlatka | |
| 7,602,883 B2 | 10/2009 | Joseph et al. | |
| 2003/0007991 A1 | 1/2003 | Masters | |
| 2003/0081732 A1 * | 5/2003 | Broyles et al. | 378/162 |
| 2005/0004581 A1 | 1/2005 | Astrom | |
| 2005/0165301 A1 | 7/2005 | Smith et al. | |
| 2005/0215874 A1 | 9/2005 | Wang et al. | |
| 2006/0293581 A1 | 12/2006 | Plewes et al. | |
| 2008/0021313 A1 | 1/2008 | Eidenschink et al. | |
| 2008/0269600 A1 | 10/2008 | Csavoy et al. | |
| 2012/0302863 A1 | 11/2012 | O'Neill et al. | |

FOREIGN PATENT DOCUMENTS

| | | |
|---|---|---|
| JP | 10290797 | 11/1998 |
| JP | 11169363 | 6/1999 |
| JP | 3065768 | 2/2000 |
| JP | 2005021700 | 1/2005 |
| JP | 2013518630 | 5/2013 |
| WO | 2005079878 | 9/2005 |
| WO | 2011/094833 A1 | 8/2011 |

OTHER PUBLICATIONS

CA2,858,657 , "Office Action", mailed Nov. 23, 2015, 4 pages.
CN201280069236.X , "Office Action", mailed Dec. 2, 2015, 9 pages.
JP2014-546055 , "Notice of Allowance", mailed Dec. 3, 2015, 3 pages.
JP2014-546055 , "Office Action", mailed Apr. 24, 2015, 7 pages.

* cited by examiner

BIOPSY GRID

BACKGROUND OF THE INVENTION

Marking grids are used during medical imaging procedures to provide visual reference points on the resulting image. The marking grid contains a contrast agent that is visible on images produced by the imaging technology employed, for example, X-rays, computerized tomography (CT) scans and/or magnetic resonance imaging (MRI). Marking grids can be used to locate the position of internal structures in the body of a patient, such as abnormal tissues or tumors, relative to the reference marks on the image. In use, the marking grid is attached to the external surface or skin of a patient's body, and the patient and marking grid are exposed to imaging radiation. The contrast agent in the marking grid produces dots, lines, or other shapes on the image that can be used as reference points.

Marking grids are useful for locating the position on the surface of a patient where a biopsy needle should be inserted. The grids typically include a radiopaque material, arranged in strips, mounted on a radio translucent border or frame. The grids are typically placed on the skin of the patient and a cross section of the grid is visible on a CT scan. The technician can determine a position for insertion of a needle by viewing the grid pattern, visible on the CT scan at the patient's skin as a series of dots representing a cross section of the strips, and inserting the needle in the appropriate location relative to the grid pattern. However, one issue with prior marking grids is that the strips on the grids often blocked access to the appropriate location on the patients skin, requiring that the marking grid be moved in order to mark the location with a skin marker prior to inserting the biopsy needle.

The present invention provides a biopsy grid in which each individual reference strip can be easily removed by the medical technician without having to move the grid, which allows for precise positioning of the biopsy needle on the surface of the patient. The present invention also provides an improved manufacturing method for making marking grids, and improved materials for use in the radio-opaque strip material.

The following references may be relevant to the present disclosure: U.S. Pat. Nos. 7,086,172; 6,714,628; 6,356,621; 5,285,785; 5,052,035; 4,985,019; 3,547,121.

BRIEF SUMMARY OF THE INVENTION

Embodiments herein provide compositions and methods useful in identifying the location of a marker relative to a tissue of interest in medical images. In one aspect, the invention provides a grid that is useful in performing biopsy procedures. In some embodiments, the grid is adapted to be arranged on a patient's skin to provide positioning information in a medical imaging procedure. In one embodiment, the grid comprises a) a frame comprising a top and bottom surface; b) a hydrogel layer attached to the top of the frame and having a top and bottom surface and comprising a mixture of a hydrogel and a contrast agent; and c) an adhesive layer on the bottom surface of the frame. The adhesive may be a low tack, releasable adhesive, and is used to attach the grid to a patient during imaging. A release liner may be provided on the bottom of the adhesive, and may be removed just prior to attaching the grid to a patient. The grid includes reference lines formed by the hydrogel layer.

In some embodiments, the grid comprises a contrast agent that is selected from a radiopaque material or a material visible in a magnetic resonance image.

In some embodiments, the grid further has a top sheet contacted to a top surface of the hydrogel layer. The top sheet is provided on the top surface of the hydrogel layer to reduce the possibility of the hydrogel drying during shipping and storage. The top sheet covers the hydrogel, and is removed, for example by a tab, just prior to use of the grid.

In some embodiments, the frame comprises a support material selected from polyester, polypropylene, polyethylene, nylon, paper or other suitable radio translucent and rigid or semi-rigid materials. The composition of the hydrogel may provide sufficient tack for the hydrogel to stick directly to the frame. In some embodiments, to aid in adhesion of the hydrogel to the frame, the top surface of the support frame is coated with an adhesive for attaching the hydrogel to the frame.

In some embodiments, the silicone release liner further comprises a pull tab.

In some embodiments, the grid has a feature on one side (e.g., the left hand side) that distinguishes that side from other sides during imaging.

In another aspect, embodiments herein provide a method of imaging a tissue of interest in a subject. For example, in some embodiments, the method comprises positioning the biopsy grid described above to the external surface or skin of the subject external to the tissue of interest; and observing the location of the biopsy grid markers relative to the tissue of interest by at least one of X-ray, CT scan, mammography, or MRI. In some embodiments, the biopsy grid is affixed to the skin of the subject by the adhesive layer. In some embodiments, the subject is an animal or human subject.

In another aspect, the invention provides a method of manufacturing a biopsy grid. In some embodiments, the manufacturing method comprises the steps of a) combining at least one contrast agent with a hydrogel to form a mixture, b) contacting the hydrogel mixture with a carrier sheet, c) curing the hydrogel mixture on a carrier sheet, d) attaching the hydrogel and carrier sheet to a frame, and e) cutting the hydrogel to a grid pattern. An adhesive layer may then be provided on the bottom of the frame, and a silicone-coated release liner may be placed over the adhesive.

DEFINITIONS

The term "hydrogel" refers to a gel comprising a network of polymer chains that are water-insoluble, in which water is the dispersion medium.

The term "release liner" refers to a layer, in embodiments comprising silicone coated polyethylene, that may be used to releasably cover the adhesive layer of the grid, and protects the adhesive layer and the exposed hydrogel from drying prior to use. The silicone release liner is typically removed from the adhesive layer prior to application of the grid to the skin of the subject undergoing an imaging procedure.

The term "adhesive layer" refers to a layer comprising a non-toxic medical grade adhesive that is suitable for affixing the grid to the skin of a subject. In some embodiments, the adhesive layer is made of acrylic.

The term "contrast agent" refers to a radiopaque substance used in radiography to enhance the contrast of an image. Non-limiting examples of radiopaque materials include a metal such as tungsten or similar metal powder, a metallic salt such as barium sulfate or calcium carbonate, a halogen such as iodine, or any other suitable radiopaque material. Non-limiting examples of contrast agents suitable for MRI include a paramagnetic material, a fatty oil such as mineral oil, vegetable oil, or fish oil, or other suitable materials and combinations thereof. As examples, the paramagnetic material may be ferric chloride, ferric ammonium citrate, gadolinium or an ion thereof, such as gadolinium(III). In some embodiments, the gadolinium is complexed with a chelating agent, such as DTPA.

The term "radiopaque material" refers to a material that at least partially attenuates or blocks transmission of X-rays.

The term "location of the marker relative to the tissue of interest" refers to the spatial orientation or relationship between the marker and the tissue of interest. The tissue of interest can have a medical feature that is being examined by an imaging procedure, for example an abnormal tissue or tumor. Depending on the imaging technology employed, the spatial relationship between the marker and the tissue of interest can be displayed in two or three dimensions.

DETAILED DESCRIPTION OF THE INVENTION

Embodiments herein provide a grid 10 that is useful for determining a scanning or imaging position during a medical imaging procedure, such as an X-ray, CT scan, or MRI procedure. In some embodiments, the grid is useful in performing a biopsy procedure.

Figure 1:
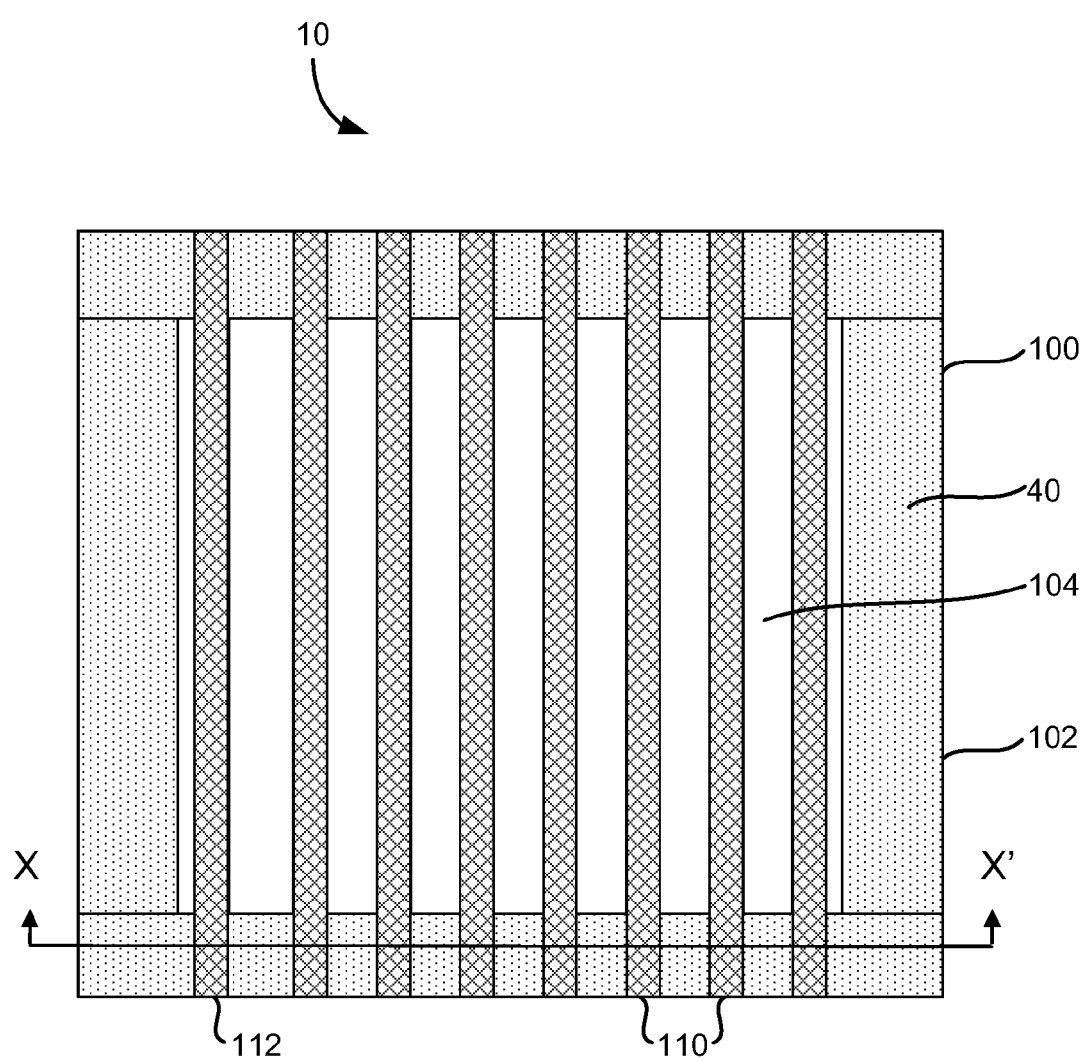
FIG. 1 shows a top, diagrammatic view of one illustrative example of a biopsy grid.
Figure 2:
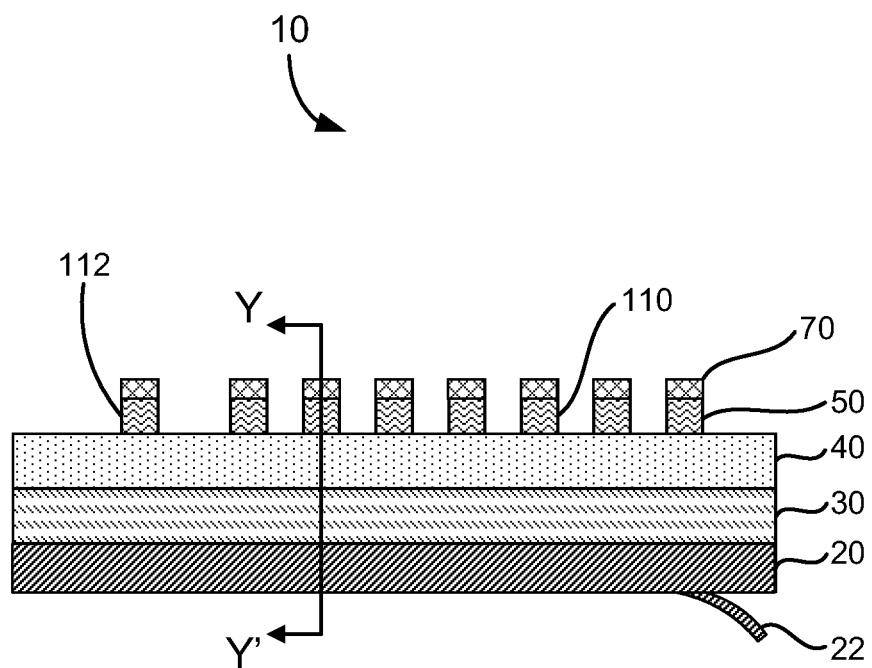
FIG. 2 shows a traverse section along plane X-X' of the biopsy grid of FIG. 1, with optional top sheet illustrated.
Figure 3:
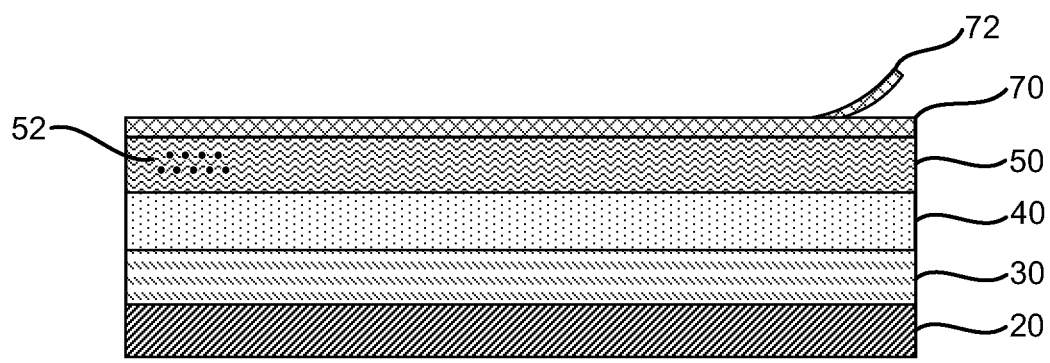
FIG. 3 shows a longitudinal section of the biopsy grid along plane Y-Y' in FIG. 2.

As shown in the embodiments illustrated in FIGS. 1-3, the grid 10 includes a frame 100 having a support layer 40. The frame includes an outer perimeter 102 with a central opening 104. In the embodiment shown in the drawings, the frame is rectangular in shape, but the frame may be shaped in other configurations. The support layer 40 can be made of a wide range of materials such as paper, polyethylene, polypropylene, nylon or a combination of the above materials, or other suitable materials known to one of skill in the art. Suitable support materials should be selected so as not to cast a shadow or create other artifacts in the image.

The support layer 40 can be coated with an adhesive to form an adhesive layer 30. The adhesive layer 30 may be, for example, a low tack acrylic based adhesive made of medical grade adhesive suitable for releasably securing the frame to the skin of a subject, such as an animal or human patient. A release liner 20 may be used to cover the adhesive layer 30 to prevent drying of the adhesive and the hydrogel prior to use. The release liner 20 may be provided with a pull tab 22 for easy removal. The release liner is widely available from many suppliers (e.g., Avery Dennison, Brea, Calif.) and is typically polyethylene material coated on one side with silicone.

Referring to FIGS. 2 and 3, the grid also has a hydrogel layer 50 positioned over at least a portion of the top of the frame 100. The hydrogel layer 50 is formed from a mixture of hydrogel and at least one contrast agent 52. The contrast agent may be, for example, a radiopaque material, a material visible in a magnetic resonance image, and a material visible in a positron emission tomograph. In embodiments, the contrast agent includes barium. The hydrogel layer is provided as strips, and the strips attach to opposite sides of the frame and extend over the central opening.

The hydrogel layer 50 typically has a top protective sheet 70 in contact with the upper surface of the hydrogel mixture. The top sheet 70 is provided on the top surface of the hydrogel layer 50 to reduce the possibility of the hydrogel drying during shipping and storage. The top sheet 70 can have a pull tab 72 for easy removal.

Methods of Manufacturing the Grid of the Invention

To assemble the grid 10, hydrogel is mixed with the contrast agent and the hydrogel is cured. The contrast agent is added to the gel by agitation during a formulation process. Conventional mixers are used for agitation.

The mixed hydrogel and contrast agent are coated onto a carrier sheet 70 in an uncured state. The carrier sheet functions to support the hydrogel before and after it is cured. As described below, the carrier sheet becomes the top protective layer 70 in the final grid. In some embodiments, the carrier sheet is made of a non-silicone coated polyethylene sheet. However, one of skill will understand that other materials suitable for use as a carrier sheet can be used. The hydrogel mixture is then cured, typically by exposing the mixture to UV light.

After curing, the hydrogel layer and the carrier sheet are laminated to the adhesive frame 100. The frame 100 is die cut from a sheet to remove the center section (the center opening 104). The carrier sheet 70 is inverted when applied to the adhesive frame, such that the carrier sheet becomes the top protective sheet 70. The hydrogel and top sheet are then die cut to form the strips. As shown in FIG. 2, the linear strips of the hydrogel define raised strips that serve as reference lines 110 when viewed from above (See FIG. 1). As shown in FIG. 1, in some embodiments, the reference lines 110 can be spaced farther apart on one side of the frame, allowing the orientation (e.g., left-right orientation) of the grid to be determined in the image. For example, as shown in FIG. 1, all but the leftmost strip 112 of hydrogel 50 are spaced equidistantly, and the leftmost strip 112 is space further apart, thus providing a reference during imaging. Other features can be added to the grid to provide spatial orientation as needed.

The support layer 40 is typically purchased with the adhesive layer 30 coated to the surface. The support layer 40 precoated with the adhesive layer 30 can be purchased from many vendors, for example Avery Dennison (Brea, Calif.) or 3M (St. Paul, Minn.). The release layer 20 is then placed against the adhesive layer 30 to protect the adhesive from drying out or sticking to something else.

Methods of Using the Grid of the Invention

The invention further provides methods for using the biopsy grid described herein. In some embodiments, the method comprises the steps of positioning the biopsy grid on the external surface or skin of an animal or human subject. The bottom release liner is removed by gripping the pull tab 22 and pulling the liner away, thereby exposing the adhesive 30. The grid is attached to the skin of the subject, frame side down, using the adhesive.

The subject is then exposed to imaging radiation, such as X-rays, CT, or MR, and an image is generated either on film or digitally. The image includes the tissue of interest and the grid, which is visible due to the presence of one or more types of contrast agents 52 in the hydrogel reference lines. A typical CT scan produces an image of a transverse slice of the subject or tissue of interest, and the reference lines will appear as spots.

Figure 4:
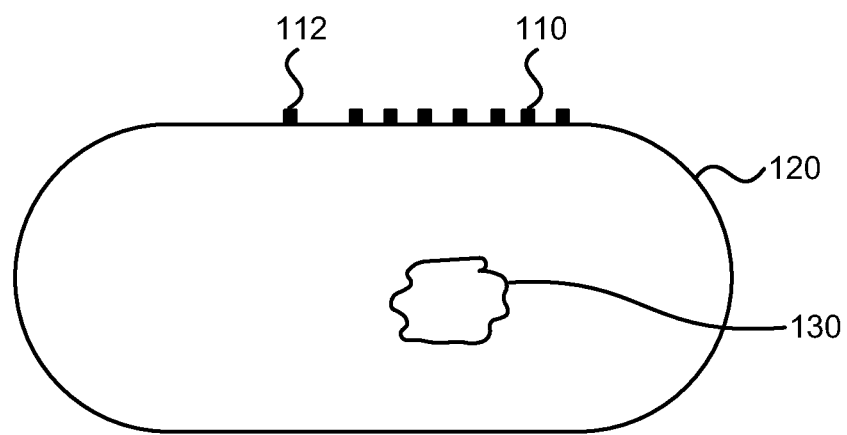
FIG. 4 is a schematic illustration of how a biopsy grid would appear in an image obtained from a CT scan.

FIG. 4 shows a schematic illustration of a CT scan image using the biopsy grid. As shown in FIG. 4, the grid is placed on the skin 120 of a patient undergoing a CT scan of a tissue of interest 130. In the image, reference lines 110 of the grid show up as circles, squares or other shapes that correspond to the cross-sectional shape of the hydrogel strips of the grid. As described a above, the reference line 112 can be spaced further apart than the other strips to permit orientation of the position of the strips in the image.

The grid reference lines provide the skilled person a marker for localizing the spot on the surface of the patient where a procedure should be performed, for example, where a biopsy needle should be inserted. Unlike prior grids, the individual reference lines of the hydrogel are flexible and/or are removably attached to the frame. Thus, the strips can be easily stretched so that they move to one side, or can be removed by a skilled technician, allowing a needle to be inserted under the marked reference line if necessary.

Examples of Hydrogel Formulations

In embodiments, the hydrogel herein may be formed in accordance with PCT publication number WO 2005/079878, "Bioadhesive Compositions and their use in Medical Electrodes", incorporated herein in its entirety. The composition of the hydrogels described therein are referred to herein as "bioadhesive hydrogels." Details of the hydrogels can be found in that reference, but some of the information from that reference is repeated here for the convenience of the reader.

Conductive soft bioadhesive hydrogels typically have high water content. Bioadhesive hydrogels formed in accordance with WO 2005/079878 are not controlled by the water content of the hydrogel, but by the chemical composition of the formulation, in particular the type and level of monomer(s) and plasticizer(s), and in which the architecture of the polymer network developed and thus the physical properties of the hydrogel depend on the type and level of monomers and plasticizer(s) being used. This allows the development of soft, skin friendly, electrically conductive bioadhesive hydrogels.

WO 2005/079878 describes that bioadhesive hydrogels are obtainable by polymerizing an aqueous mixture of two or more water-soluble monomers, aqueous plasticizer and cross-linking agent. In particular, acrylic acid is a water-soluble monomer that is commonly used in the development of pressure sensitive adhesives, hydrogels and bioadhesive hydrogels. Copolymerization of acrylic acid with sodium acrylamido tertiary butyl sulfonate (NaAMPS or ATBS-Na) produces hydrogels with useful properties. ATBS-Na is sold as a 50% or 58% solution in water and the available materials provide a useful source of both monomer and water. The total level of the water in the formulation, and hence water content in the final hydrogel can be controlled by the amount of ATBS-Na (as 50% or 58% solution) in the formulation as no water is removed during the processing stage.

WO 2005/079878 also describes a bioadhesive composition comprising: (i) 28-60 weight percent (e.g. 32-52 wt %) of a copolymer comprising repeating units derived from one or more monomers selected from olefinically unsaturated sulphonic acids and repeating units derived from one or more olefinically unsaturated carboxylic acids, the ratio by weight of the sulphonic acid units to the carboxylic acid units being from 30:1 to 1:1; (ii) 20-45 wt % (e.g. 25-45 wt %) of plasticizer(s); and (iii) 10-55 wt % (e.g. 10-35 wt %) of water; the balance being electrolyte (if any) and optional ingredients.

WO 2005/079878 further describes a bioadhesive composition comprising: (a) 28-60 wt % (e.g. 32-52 wt %) of a polymer based on repeating units derived from one or more monomers selected from olefinically unsaturated sulphonic acids; (b) 20-45 wt % (e.g. 25-45 wt %) of plasticizer(s); (c) 10-55 wt % (e.g. 10-35 wt %) of water; and (d) at least one of an alkoxy polyethyleneglycol acrylate or methacrylate, p-carboxyethyl acrylate, acryoyl oxyethyl trimethyl ammonium chloride or 3-acrylamidopropyl trimethyl ammonium chloride, the balance being electrolyte (if any) and optional ingredients.

WO 2005/079878 additionally describes a bioadhesive composition comprising: (a) a copolymer comprising repeating units derived from (i) one or more monomers selected from olefinically unsaturated sulphonic acids (ii) one or more olefinically unsaturated carboxylic acids, the ratio by weight of the sulphonic acid units to the carboxylic acid units being from 30:1 to 1:1; (b) a water-soluble polyhydric alcohol that is liquid at ambient temperatures; (c) a mono- or di-ester of polyethylene glycol with a fatty acid e.g. lauric, myristic, palmitic, stearic, oleic, arachidic or erucic acid; and (d) water.

WO 2005/079878 even further describes a bioadhesive composition comprising: (a) a copolymer comprising repeating units derived from (i) one or more monomers selected from olefinically unsaturated sulphonic acids (ii) one or more olefinically unsaturated carboxylic acids, the ratio by weight of the sulphonic acid units to the carboxylic acid units being from 30:1 to 1:1, and (iii) p-carboxyethyl acrylate; (b) at least one plasticizer; and (c) water.

WO 2005/079878 still even further describes uncured compositions for UV-curing into any of the above, e.g. an uncured composition including as photoinitiator a mixture of an oligomeric a-hydroxyketone and 2-hydroxy-2-methyl-1-phenyl-1propanone.

In any event, WO 2005/079878 describes several different bioadhesive hydrogel compositions having desired qualities for use in present embodiments. In general, the bioadhesive hydrogels are soft, flexible, compatible with skin of subjects, and are not prone to drying during storage or prior to use.

In some embodiments, the hydrogel of the invention comprises the ingredients shown in Table 1.

TABLE 1

| Hydrogel Formulation | |
|---|---|
| Glycerin | 47.00% |
| SATBS | 12.00% |
| Acrylic Acid | 24.00% |
| NaOH | 1.35% |
| Propylparaben | 0.17% |
| methylparaben | 0.80% |
| Barium Sulfate | 6.00% |
| HEC | 0.15% |
| Irgacure 651 | 0.16% |
| Irgacure2959 | 0.70% |
| v-pyrol | 2.80% |
| EDGMA | 0.20% |
| IPA 99% | 0.11% |
| RO water | 5.00% |

It will be understood that the invention is not limited to the formula of Table 1, and that different formulations with equivalent ingredients having the desired functional characteristics are within the scope of the invention.

In some embodiments, the barium sulfate can be varied from 3 to 10% to vary the opacity of the marker. In some embodiments, the biopsy grid is to be used for MRI, and the formula of Table 1 can have the following changes: barium sulfate is removed and gadolinium or other contrast agent is added. The amount of glycerin can be adjusted depending on the amount of gadolinium added.

In some embodiments, the biopsy grid can be used as a multi-modal marker (i.e., available for imaging in multiple modes of imaging), and the formula of Table 1 is modified to add a suitable quantity of MRI contrast agent, which is in the range of about 6% or less. Suitable contrast agents for MRI include a paramagnetic material, a fatty oil such as mineral oil, vegetable oil, or fish oil, or other suitable materials and combinations thereof. As examples, the paramagnetic material may be ferric chloride, ferric ammonium citrate, gadolinium or an ion thereof, such as gadolinium(III). In some embodiments, the gadolinium is complexed with a chelating agent, such as DTPA.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of manufacturing a biopsy grid, the grid adapted to be arranged on a patient's skin to provide positioning information in a medical imaging procedure, the method comprising the steps of:
   a) combining at least one contrast agent with a hydrogel to form a mixture, the hydrogel providing sufficient tack to stick directly to a frame and the at least one contrast agent visible in the medical imaging procedure, wherein the frame comprises a top and a bottom surface and a central opening;
   b) coating the mixture onto a carrier sheet in an uncured state;
   c) curing the mixture;
   d) cutting hydrogel strips after curing; and
   e) releasably attaching the hydrogel strips to opposite sides of the frame extending across the central opening of the frame so that, in use, the hydrogel strips can be moved by a medical technician from the frame, when the frame is attached to the patient's skin, so that an area underneath the hydrogel strips may be accessed to provide the positioning information without removing the frame from the patient's skin.

2. The method of claim 1, wherein the at least one contrast agent is selected from a radiopaque material or a material that is visible on an X-ray image.

3. The method of claim 2, wherein the radiopaque material comprises at least one material selected from the group consisting of tungsten, barium sulfate, calcium carbonate and iodine.

4. The method of claim 1, wherein the at least one contrast agent is a combination of materials such that the contrast agent is visible in an X-ray image, an MRI image and/or a CT image.

5. The method of claim 1, wherein the at least one contrast agent is selected from a paramagnetic material or a material visible in a magnetic resonance image (MRI).

6. The method of claim 5, wherein the paramagnetic material comprises at least one material selected from the group consisting of ferric chloride, ferric ammonium citrate and gadolinium.

7. The method of claim 1, further comprising a top sheet contacted to a top surface of the hydrogel strips.

8. The method of claim 1, wherein the frame comprises a support material selected from polyester, polypropylene, polyethylene, nylon, and paper.

9. The method of claim 1, further comprising an adhesive layer on the bottom of the frame for releasably adhering to the patient's skin.

10. The method of claim 9, further comprising a release liner extending over the adhesive layer.

11. The method of claim 10, wherein the release liner comprises a pull tab.

12. A method of imaging a tissue of interest, the method comprising:
   a) positioning the biopsy grid manufactured according to the steps of claim 1 on the patient's skin external to the tissue of interest; and
   b) observing the location of the biopsy grid relative to the tissue of interest by at least one of X-ray, CT scan, mammography, MRI or positron emission tomography.

13. The method of claim 12, further comprising:
reversibly detaching the hydrogel strip from a location on the frame while the biopsy grid remains positioned against the patient's skin; and
inserting a biopsy needle into the patient at the location where the detached hydrogel strip was previously located.

14. The method of claim 12, further comprising:
reversibly removing a portion of the hydrogel strip from a location on the frame while the biopsy grid remains positioned against the patient's skin; and
inserting a biopsy needle into the patient at the location where the portion of the hydrogel strip was previously located.

15. A method of making a grid, the grid adapted to be arranged on a patient's skin to provide positioning information in a medical imaging procedure, the method comprising the steps of:
   a) combining at least one contrast agent with a hydrogel to form a mixture, the hydrogel providing sufficient tack to stick directly to a frame and the at least one contrast agent visible in the medical imaging procedure, wherein the frame comprises a top and a bottom surface and a central opening;
   b) coating the mixture onto a carrier sheet in an uncured state;
   c) curing the mixture to at least a semi-rigid state;
   d) cutting the cured mixture into hydrogel strips; and
   e) releasably attaching the hydrogel strips to opposite sides of the frame and extending across the central opening of the frame so that, in use, the hydrogel strips can be reversibly displaced from a first position on the frame to a second position on the frame by a medical technician without moving the frame when the frame is attached to the patient's skin to allow access to a treatment site on the patient's skin for precise placement of a biopsy needle, the placement based on the positioning information in the medical imaging procedure and further allowing the hydrogel strips to return to the first position after the biopsy needle has been removed from the treatment site.

\* \* \* \* \*